United States Patent
Lugli et al.

(10) Patent No.: US 10,145,838 B2
(45) Date of Patent: Dec. 4, 2018

(54) DEVICE FOR ANALYZING BIOLOGICAL SUBSTANCES IN A TEST SOLUTION AND PRODUCTION METHOD

(71) Applicant: Technische Universität München, Munich (DE)

(72) Inventors: Paolo Lugli, Hallbergmoos (DE); Vijay Deep Bhatt, Munich (DE); Katharina Melzer, Moorenweis (DE)

(73) Assignee: Technische Universität München, Munich (DE)

( * ) Notice: Subject to any disclaimer, the term of this patent is extended or adjusted under 35 U.S.C. 154(b) by 0 days.

(21) Appl. No.: 15/281,772

(22) Filed: Sep. 30, 2016

(65) Prior Publication Data
US 2017/0097331 A1 Apr. 6, 2017

(30) Foreign Application Priority Data
Oct. 1, 2015 (DE) .......................... 10 2015 219 023

(51) Int. Cl.
*G01N 33/487* (2006.01)
*G01N 27/02* (2006.01)
(Continued)

(52) U.S. Cl.
CPC ...... *G01N 33/48707* (2013.01); *B01L 3/5027* (2013.01); *G01N 15/1031* (2013.01);
(Continued)

(58) Field of Classification Search
CPC .............................................. G01N 33/48707
See application file for complete search history.

(56) References Cited

U.S. PATENT DOCUMENTS

| 6,437,551 B1 * | 8/2002 | Krulevitch ......... G01N 33/5438 324/649 |
| 2004/0189311 A1 * | 9/2004 | Glezer ................. B01L 3/5027 324/444 |

(Continued)

FOREIGN PATENT DOCUMENTS

| WO | 2004010103 A2 | 1/2004 |
| WO | 2014124365 A2 | 8/2014 |

OTHER PUBLICATIONS

Park, Dong-Wook, et al., "Graphene-based carbon-layered electrode array technology for neural imaging and optogenetic applications," Nature Communications Article, published Oct. 20, 2014 (86 pages).
(Continued)

*Primary Examiner* — Clayton E LaBalle
*Assistant Examiner* — Jas Sanghera
(74) *Attorney, Agent, or Firm* — Maginot, Moore & Beck, LLP

(57) ABSTRACT

The invention relates to a device (100; 200; 300; 400) for analyzing biological substances in a test solution, comprising a test substrate (101; 203; 303; 401) which is transparent at least in part, having a test region (107a, 108a, 109a, 110a; 211; 411) for receiving the test solution, a plurality of electrodes (111, 106; 201, 202; 301, 302; 402, 403) which are arranged on the test substrate (101; 203; 303; 401) and extend into the test region (107a, 108a, 109a, 110a; 211; 411), wherein in each case, at least one portion of the electrodes (111, 106; 201, 202; 301, 302; 402, 403) is made of a transparent material.

14 Claims, 9 Drawing Sheets

(51) Int. Cl.
  *G01N 27/30* (2006.01)
  *G01N 15/14* (2006.01)
  *G01N 33/483* (2006.01)
  *B01L 3/00* (2006.01)
  *G01N 15/10* (2006.01)

(52) U.S. Cl.
  CPC ....... *G01N 15/1468* (2013.01); *G01N 27/026* (2013.01); *G01N 27/305* (2013.01); *G01N 33/4836* (2013.01); *G01N 33/48735* (2013.01); *B01L 2300/0645* (2013.01); *B01L 2300/0654* (2013.01); *B01L 2300/0816* (2013.01); *B01L 2300/163* (2013.01); *G01N 2015/1006* (2013.01)

(56) References Cited

U.S. PATENT DOCUMENTS

| | | |
|---|---|---|
| 2011/0100820 A1 | 5/2011 | Bachmann et al. |
| 2012/0091003 A1 | 4/2012 | Chuang et al. |
| 2012/0190040 A1 | 7/2012 | Talebpour et al. |
| 2012/0190589 A1 | 7/2012 | Anderson et al. |
| 2012/0235080 A1 | 9/2012 | Hong et al. |
| 2012/0244572 A1 | 9/2012 | Greenbaum et al. |
| 2012/0325665 A1 | 12/2012 | Chiou et al. |
| 2013/0030510 A1 | 1/2013 | Han et al. |
| 2013/0114120 A1 | 5/2013 | Jung et al. |
| 2013/0126358 A1 | 5/2013 | Lee et al. |
| 2013/0260447 A1 | 10/2013 | Link |
| 2014/0057283 A1 | 2/2014 | Wang et al. |
| 2014/0278136 A1 | 9/2014 | Shamsheyeva et al. |
| 2014/0305799 A1 | 10/2014 | Link et al. |
| 2014/0363823 A1 | 12/2014 | Goldberg et al. |
| 2015/0008123 A1 | 1/2015 | Cheng et al. |
| 2015/0107998 A1 | 4/2015 | Fobel et al. |
| 2015/0174577 A1 | 6/2015 | Srinivasan et al. |

OTHER PUBLICATIONS

European Search Report corresponding to German application No. 16191896.6, dated Nov. 1, 2017 (12 pages).

\* cited by examiner

DEVICE FOR ANALYZING BIOLOGICAL SUBSTANCES IN A TEST SOLUTION AND PRODUCTION METHOD

This application claims priority under 35 U.S.C. § 119 to patent application no. DE 10 2015 219 023.4, filed on Oct. 1, 2015 in Germany, the disclosure of which is incorporated herein by reference in its entirety.

The present invention relates to a device for analysing biological substances in a test solution and to a production method for a device for analysing a test solution.

Efficient and precise methods for examining cells are of paramount importance in numerous areas of application in biology, medicine or pharmacy. Such methods include in particular identifying specific cell components, for example of DNA, proteins or enzymes, or examining the changeability of said cell components in order to draw conclusions about the vitality of cells or the growth of cells. Such analyses are used for example to examine the quality of food or water, for drug trials and toxicity studies.

Conventional methods for examining cells, of the type which are also used to develop in vitro cell models for toxicology tests and drug and clinical trials are visual examination methods in this case. For this purpose, conventionally parts of the cells are marked with fluorescent molecules, chromophores, fluorescent dyes or radioactive molecules in order to be able to better examine said cell components. As a result, however, specific chemical or biological properties of the cell components to be examined can be changed, and this makes precise examination more difficult.

Electrical methods, in particular impedance spectroscopy, offer alternatives to examining fluidic microsystems. DE 102 34 487 A1 discloses an impedance measuring method for particles suspended in a liquid. In this case, an electrical field is created between electrodes, and by measuring the change in impedance of the electrodes, it is possible to draw conclusions about moving particles between the electrodes, since said particles interact with the electrical field.

The electrodes typically consist of metals such as gold, which leads to the electrodes being visually opaque. As a result, it is not possible to apply visual methods at the same time.

The present invention provides a device for analysing biological substances in a test solution according to claim 1.

Accordingly, the present invention provides a device for analysing biological substances in a test solution, comprising a test substrate which is transparent at least in part and has a test region for receiving the test solution. Furthermore, the device comprises a plurality of electrodes which are arranged on the test substrate and extend into the test region, wherein in each case, at least one portion of the electrodes is made of a conductive and transparent material in the test region.

A "test solution" is understood to mean in particular a microfluid. The test solution can contain multicomponent substances, for example the test solution can be blood.

The term "material" in this case refers to both a single-component and a multicomponent material. In particular, the electrodes can include various portions which are produced from different components.

In this case, "transparency" means that there is a transmission of more than 50%, in particular more than 70%, preferably more than 90% in a corresponding wavelength range of the electromagnetic radiation. In this case, the corresponding wavelength range can include in particular visible light. In particular, the wavelength range of the electromagnetic radiation lies in a visible spectral range of between 350 nm and 800 nm. However, the wavelength range can also extend into the ultraviolet range and/or infrared range.

The electrodes consist at least in part of a conductive material.

Furthermore, the present invention provides a production method for a device for analysing biological substances in a test solution having the features from claim 11.

The invention accordingly provides a production method for a device for analysing biological substances in a test solution comprising the steps of: forming a test substrate which is transparent at least in part, preferably is completely transparent, and has a test region for receiving the test solution; and arranging a plurality of electrodes on the test substrate. In this case, at least one portion of the electrodes in each case is made of a transparent material in the test region.

The device according to the invention has the advantage that the electrodes are transparent in at least some portions, as a result of which the device is suitable both for analysing biological substances in the test solution by means of impedance spectroscopy and for analysing by means of visual methods. By means of impedance spectroscopy, the biological substances can be examined in a precise manner, for example it is possible to discern whether cells or cell components are located in specific positions of the device in the test region. Furthermore, movements or the growth of individual cells, neurons, a cell layer or cell components can be measured. Electrical analysis, in particular impedance spectroscopy, has the advantage of being compact to implement. In particular, the electronics can be integrated directly in the device. In this case, the electronic evaluation provides a highly sensitive method to complement visual methods. Since the biological substances are not labelled, there is no risk of distorting the test results due to a change in the cell behaviour.

Secondly, for example by placing the device in a conventional microscope, it is possible to carry out an additional visual readout. By recording images or videos, the visual data obtained thereby can be correlated with the data obtained by means of impedance spectroscopy and evaluated together. It is thereby possible to increase the precision of the analyses. By means of a parallel visual and electrical analysis of the test solution and of the cells and/or cell components which are for example contained therein, new electrical standard tests can be developed and simultaneously correlated with conventional visual standard tests and validated thereby. As a result, the new electrical tests can be established as standard tests in different domains of biology, pharmacy or medicine. In addition to conventional impedance spectroscopy, by means of this device, new types of electrical measuring methods can also be implemented for example to determine cell movement. In this case, the device is suitable for various applications in biology, pharmacy or medicine.

According to one development of the device according to the invention, the test substrate comprises a cavity for receiving the test solution. The device can comprise in particular fluid chambers and/or a channel system and/or depressions for receiving the test solution. By using channels which have an inlet and an outlet, a simple fluid exchange or cell exchange can be made possible. In particular, it is possible to mix different substances or test solutions by for example applying specific microfluidics. This also specifically makes it possible to analyse multi-component test solutions.

According to one development of the device according to the invention, the transparent material of which at least the portion of the electrodes is made in each case includes carbon nanotubes (CNTs) and/or conductive oxides (e.g. ZnO) and/or polymers and/or metal nanowires, in particular silver nanowires, and/or PEDOT:PSS and/or graphene and/or graphene oxide. By using a suitable nanomaterial of this type, the electrical properties of the electrodes can be optimised. For example, silver nanowires have a good conductivity and at the same time are visually transparent.

According to one development of the device according to the invention, the test substrate and the electrodes consist at least in part of a biocompatible, in particular bioinert material. A bioinert material of this type includes for example polymer structures or carbon nanotubes.

A "bioinert material" in this case refers to a potentially multicomponent material, wherein the chemical and/or biological interactions between the material in the case of contact with biological substances do not occur with said material. No amounts of toxic substances are released, and therefore the bioinert material does not noticeably change or even destroy the biological substances. In the case of a biocompatible material, the interactions are merely weak, and only small amounts of toxic material are emitted.

According to one development of the device according to the invention, the electrodes each comprise an end region and a remaining region. Each end region of the electrodes consists at least in part, preferably in full, of a biocompatible, in particular bioinert material, and each remaining region of the electrodes consists of a material which has a higher electrical conductivity than the biocompatible material. By means of a hybrid structure of this type of the electrodes, said electrodes are preferably made for the most part of a material having a good electrical conductivity, for example of silver nanowires. The end region of the electrodes consists of biocompatible, in particular bioinert material, for example of carbon nanotubes. The respective end regions of the electrodes in this case extend preferably into the test region of the test substrate, and therefore in the test region, which is used to receive the biological material, the electrodes consist of a biocompatible material. As a result, the biological substances of the cells to be examined are hardly or not at all changed or influenced by the electrodes. The device of this type with a hybrid structure of the electrodes thus combines transparency, good conductivity and biocompatibility.

According to one development of the device according to the invention, the electrodes consist at least in part of a material which, when irradiated with visible light and/or UV light, does not have any fluorescence or autofluorescence and/or absorption and/or reflection and/or quenching effects, in particular fluorescence quenching. Such a device can be used in particular with conventional light microscopes and fluorescence microscopes. The incidence of light can also take place through the electrodes without influencing the measurement results by means of fluorescence, quenching, absorption or reflection of the electrode material.

According to one development of the device according to the invention, the test substrate and the electrodes consist at least in part of a bendable material. A "bendable material" in this case refers to a mechanically flexible material. In this case, the device is suitable in particular for in vivo examinations, since the shape thereof can be adapted to the structures to be examined.

According to one development of the device according to the invention, the electrodes each comprise an end region and a remaining region. The respective end regions of at least two electrodes are arranged in rows which are substantially parallel to one another in the test region. If the impedance of an end region of an electrode changes, then it can be inferred that a cell or a cell component has moved into said end region or has grown into said end region. As a result, a speed or a growth of biological substances in a direction which is perpendicular to the parallel rows inside the test region can be measured.

According to one development of the device according to the invention, the electrodes each comprise an end region and a remaining region. The respective end regions of at least two of the electrodes are arranged in the test region so as to be distributed in a spatially uniform manner, in particular in an array. By measuring changes in impedance of the electrodes in the array, a movement or growth of the biological substances within the array can be measured in the test region in a spatially and/or temporally resolved manner.

According to one development of the production method according to the invention, the electrodes are arranged by means of a spraying process and/or spin-coating and/or an ink-jet printing process and/or 3D printing. The above-mentioned processes are simple and cost-effective to carry out and do not use any harmful chemicals which could change the biological substances to be examined.

According to another aspect, the invention comprises a method for operating a device for analysing biological substances in a test solution. In a first method step, the test solution is applied to the test region of the test substrate. Subsequently, the impedances of the electrodes are measured, and the biological substances are analysed on the basis of the measured impedances of the electrodes. Analysing includes in particular determining cell movements and/or cellular growth, that is to say propagation and/or growth speeds and/or cell vitality.

According to another aspect, the invention comprises a method for operating a device for analysing biological substances in a test solution. The test solution is applied to the test region of the test substrate, the impedances of the electrodes are measured, and a propagation speed and/or a growth speed of the biological substances in the test solution in a direction which is perpendicular to the parallel rows are determined on the basis of the measured impedances of the electrodes.

According to another aspect, the invention comprises a method for operating a device for analysing biological substances in a test solution. After applying the test solution to the test region of the test substrate, impedances of the electrodes which are distributed in a grid shape are measured, and a spatial and/or temporal distribution of the biological substances, i.e. cells, in the test solution is determined on the basis of the measured impedances of the electrodes.

The present invention will be described in greater detail below on the basis of the embodiments shown in the schematic drawings of the figures,
in which.

Figure 6:
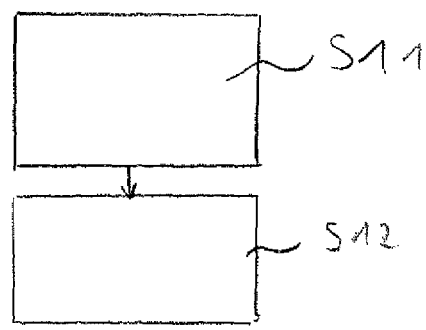
Figure 7:
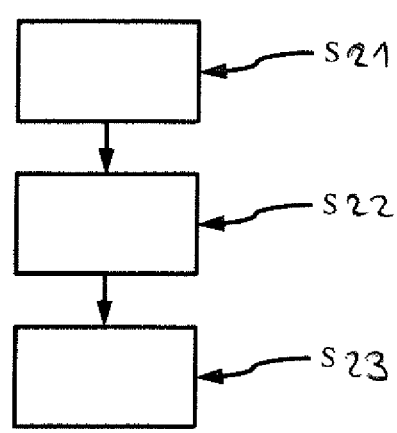
Figure 8:
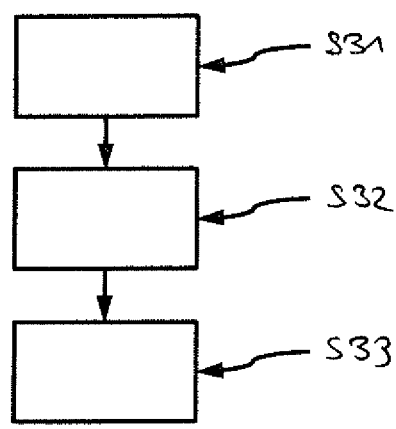
Figure 9:
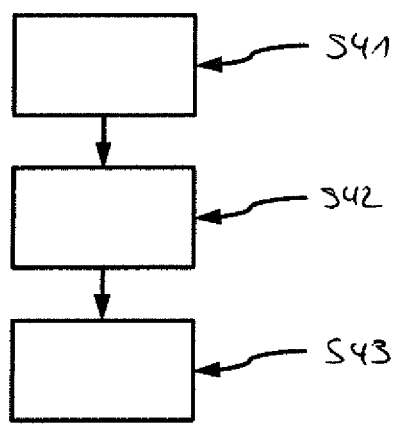

FIG. 5a-d are schematic cross-sectional views of electrode structures;

FIG. 6 is a flow chart for illustrating a production method for a device for analysing biological substances in a test solution according to one embodiment of the present invention; and FIG. 7-9 are flow charts for illustrating methods for operating a device for analysing biological substances in a test solution.

Figure 1:
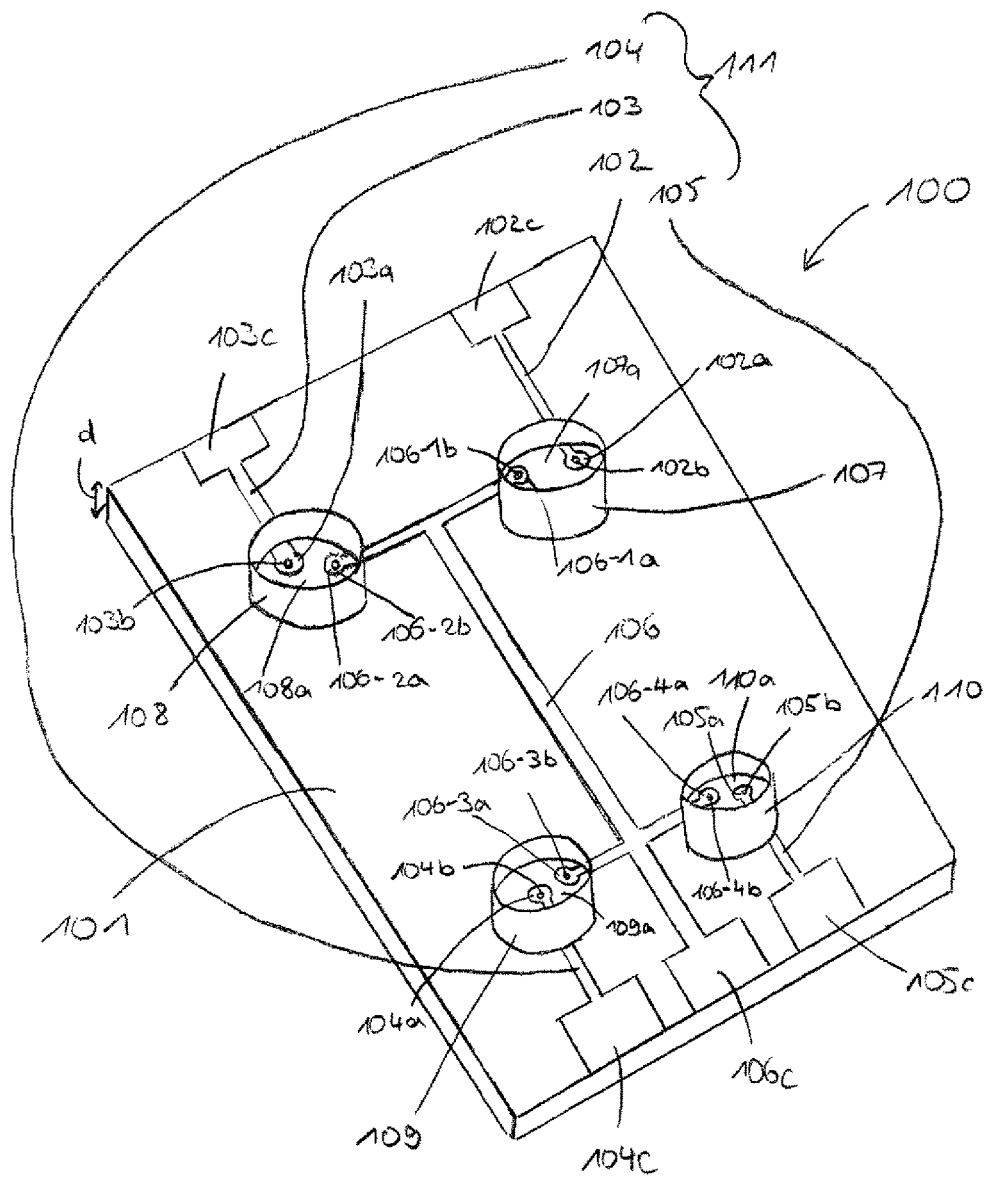
FIG. 1 shows a device for analysing biological substances in a test solution according to a first embodiment of the present invention.

FIG. 1 shows a device 100 for analysing biological substances in a test solution according to a first embodiment of the present invention.

The device 100 comprises a test substrate 101 which consists in at least some portions of a transparent material.

The test substrate 101 preferably consists of plastics material, for example PET and/or cyclic olefinic polymers (COP). However, the test substrate 101 can also be made of other materials, in particular glass and/or silk and/or paper, in particular also of film and/or plaster.

The test substrate can in particular also consist of a bendable material. A thickness d of the test substrate 101 is selected in this case to be small enough that the test substrate 101 can be bent. Preferably, the test substrate 101 consists of a biocompatible material. The biocompatible material can in particular include a bioinert material.

First to fourth fluid chambers 107, 108, 109 and 110 are arranged on the test substrate 101. In this case, the first to fourth fluid chambers 107 to 110 consist of circular annular protrusions which are attached to the test substrate 101 for example by adhesion. Preferably, the first to fourth fluid chambers 107 to 110 consist of the same material as the test substrate 101. In particular, the test substrate 101 can be made in one piece with the first to fourth fluid chambers 107 to 110.

Furthermore, first to fifth electrodes 102, 103, 104, 105 and 106 are arranged on the test substrate 101. The first to fifth electrodes 102 to 106 comprise respective contact regions 102c to 106c.

The first to fourth electrodes 102 to 105 in this case form an electrode group 111, are formed to be strip-shaped and with one arm, and comprise first to fourth end regions 102a to 105a on an end which is opposite the contact regions 102c to 105c.

By contrast with the electrode group 111, the fifth electrode 106 comprises, in addition to the fifth contact end 106c, four electrode arms with fifth to eighth end regions 106-1a, 106-2a, 106-3a and 106-4a.

The first to fourth end regions 102a to 105a of the first to fourth electrodes 102 to 105, and the fifth to eighth end regions 106-1a to 106-4a of the fifth electrode 106 are in this case each designed to be circular and each comprise in the inner region a smaller circular internal region 102b, 103b, 104b, 105b, 106-1b, 106-2b, 106-3b and 106-4b, which consists of a conductive, transparent and biocompatible, in particular bioinert material. This material preferably includes carbon nanotubes and/or conductive metal oxides and/or polymers and/or hybrids and/or metal nanowires. The remaining region of the electrodes, that is to say in particular the outer region of the circular end regions 102a to 105a and 106-1a to 106-4a, and the remaining region, which is different from the end region, of the first to fifth electrodes 102 to 106 consists of a transparent material which has a higher electric conductivity than the biocompatible material which is used for the internal regions. In particular, the material can include metal nanowires, for example silver nanowires.

However, the invention is not limited thereto. Thus the first to fifth electrodes 102 to 106 can also be produced from a single-component transparent material. Preferably, the first to fifth electrodes 102 to 106 are made of a biocompatible and/or bendable material.

The first to fourth end regions 102a to 105a of the first to fourth electrodes 102 to 105 extend into first to fourth test portions 107a, 108a, 109a and 110a which are surrounded by the first to fourth fluid chambers 107 to 109 on the test substrate 101. The first to fourth test portions 107a to 110a together form a test region on the test substrate 101 which is formed so as to receive a test solution with biological substances. A test solution of this type can be inserted for example by means of a pipette into the first to fourth test portions 107a to 110a which are surrounded by the first to fourth fluid chambers 107 to 110. The test solution can also be inserted by means of microfluidic supply lines and/or a pump system and/or automated liquid-handling systems and/or by means of a suitable surface structuring or functionalisation. Furthermore, surface acoustic waves (SAWs) are also a possible means for transporting the test solution.

The biological substances, which contain for example cells or cell components, in this case are preferably in suspension in the test solution.

The invention is not limited thereto. In particular, the number and arrangement of the electrodes and fluid chambers and the number of electrodes which each extend into a fluid chamber can vary.

Figure 2:
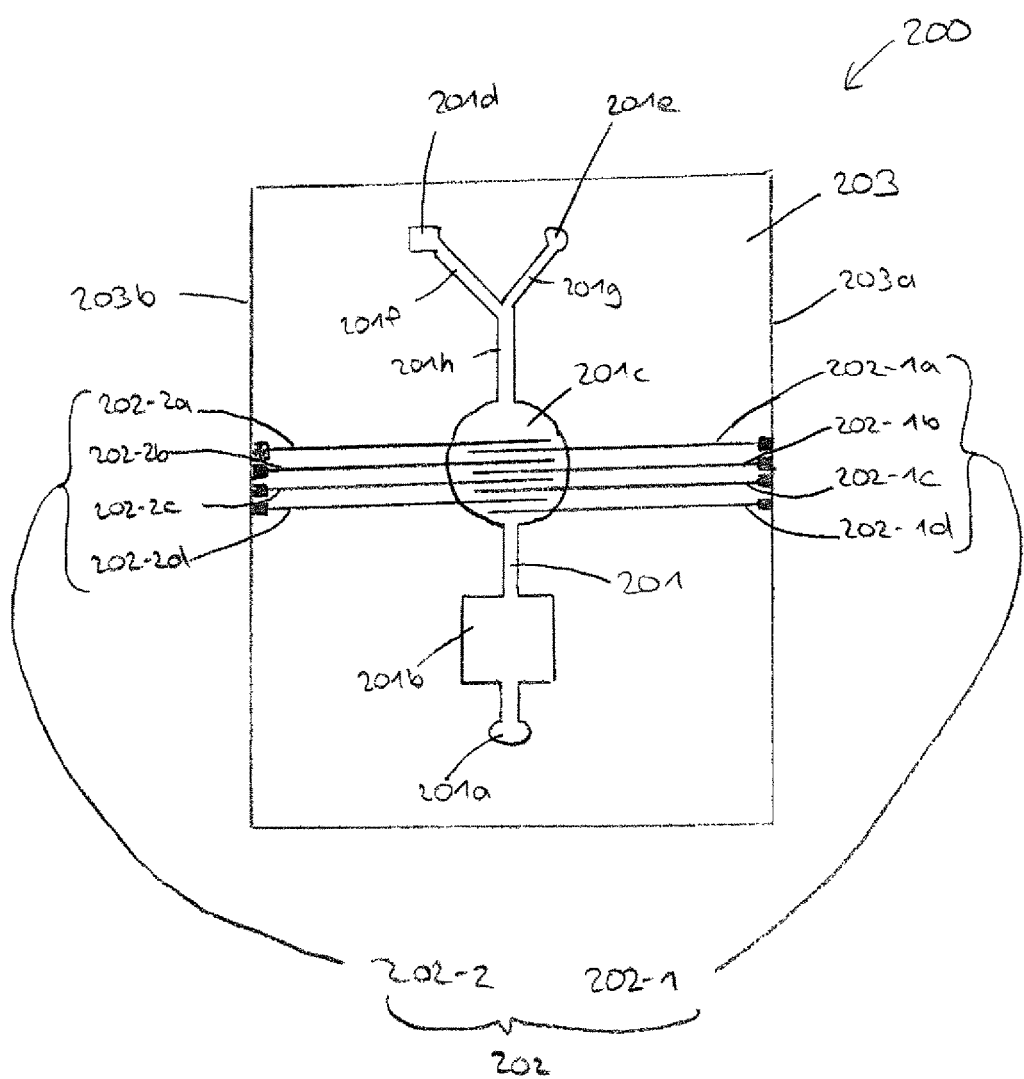
FIG. 2 shows a device for analysing biological substances in a test solution according to a second embodiment of the present invention.

FIG. 2 shows a device 200 for analysing biological substances in a test solution according to a second embodiment of the present invention. On a test substrate 203 which can consist of the same material as the test substrate 101 from the first embodiment, that is to say in particular is transparent at least in part, a microfluidic system 201 is arranged. The microfluidic system 201 is in the form of a cavity and is used to receive a test solution. The microfluidic system 201 comprises a first fluid chamber 201d and a second fluid chamber 201e for introducing (potentially different) test solutions. By means of supply lines or channels 201f, 201g and 201h, said solutions can be introduced into a third fluid chamber 201c. The microfluidic system 201 comprises an additional fourth microfluid chamber 201b and a fifth microfluid chamber 201a, which are likewise connected by supply lines to the third microfluid chamber 201c and which are designed to introduce and/or discharge and/or mix test solutions or liquids and/or substances into the third microfluid chamber 201c.

The invention is not limited thereto. The microfluidic system 201 can thus comprise a plurality of additional supply lines and/or microfluid chambers which are designed to introduce and/or mix test solutions. In this case, the microfluidic system 201 can be in the form of a channel system, wherein openings for inserting test solutions are arranged in the fluid chambers. Furthermore, electrode structures can be formed in various microfluid chambers. The device 200 can thus comprise additional electrodes which project into the fourth microfluid chamber 201. Furthermore, the fluid chambers can be any desired shape.

On the test substrate 203, a right electrode group 202-1 consisting of first to fourth electrodes 202-1a to 202-1d is arranged, which electrodes comprise contact ends on a right end 203a of the test substrate 203. On a left side 203b of the test substrate 203, which is opposite the right side 203a of the test substrate 203, are located contact ends of a left electrode group 202-2 consisting of fifth to eighth electrodes 202-2a to 202-2d. The electrodes 202 consisting of the left electrode group 202-2 and the right electrode group 202-1 in this case are formed on the test substrate in such a way that end regions of the electrodes 202, which project into the third microfluid chamber 201c, are arranged in rows which are parallel to one another.

The electrodes 202 consist of a transparent, preferably biocompatible and/or bendable material. The electrodes consist for example of carbon nanotubes (CNTs) and/or conductive metal oxides (e.g. ZnO) and/or polymers and/or metal nanowires, for example silver nanowires, and/or PEDOT:PSS and/or graphene and/or graphene oxide.

The invention is not limited thereto. In particular, the number of the electrodes 202 can be greater or smaller. Preferably, the number of the electrodes 202 can be large in order to provide a precise grid with good spatial resolution.

Figure 3:
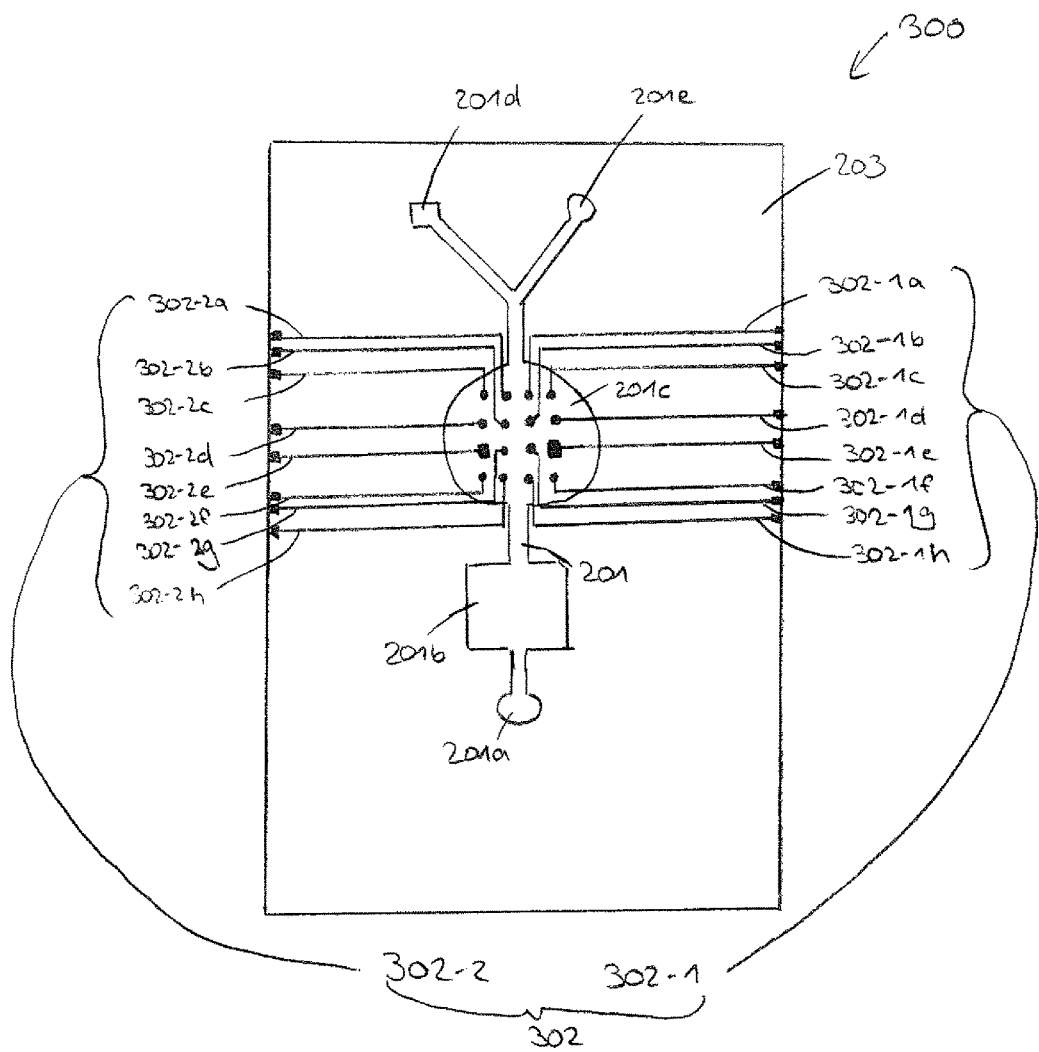
FIG. 3 shows a device for analysing biological substances in a test solution according to a third embodiment of the present invention.

FIG. 3 shows a device 300 for analysing biological substances in a test solution according to a third embodiment of the present invention. The device 300 differs from the second embodiment shown in FIG. 2 in the number and arrangement of the electrodes. The device 300 according to the third embodiment comprises electrodes 302 which are divided into a left electrode group 302-2 and a right electrode group 302-1. The right electrode group 302-1 comprises first to eighth electrodes 302-1a to 302-1h, and the left electrode group 302-2 comprises ninth to seventeenth electrodes 302-2a to 302-2h. The electrode ends of the electrodes 302, which are located in the third microfluid chamber 201c, are punctiform or rectangular (see electrodes 302-2e and 302-1e) and arranged in a symmetrical 4×4 array which is distributed in a spatially uniform manner. The electrodes in turn consist of one of the materials which have already been described above for the second embodiment. In particular, the electrodes 302 can also consist of two different material components. Thus for example those portions of the electrodes 302 which are located inside the third microfluid chamber 201c, that is to say in particular punctiform or rectangular electrode ends of the electrodes 302, can be made of a biocompatible material, preferably of carbon nanotubes and/or of a polymer, and those portions of the electrodes which do not project into the third microfluid chamber 201c can be made of a material having a higher electrical conductivity than the biocompatible material. Preferably, silver nanowires are used in this case.

The invention is not restricted to the above-mentioned number and arrangement of the electrodes. In particular, the number of the electrodes 302 can be greater or smaller. Preferably, the number of the electrodes 302 can be large in order to provide a precise grid with good spatial resolution. Furthermore, all electrode ends can be punctiform or all electrode ends can be rectangular.

Figure 4:
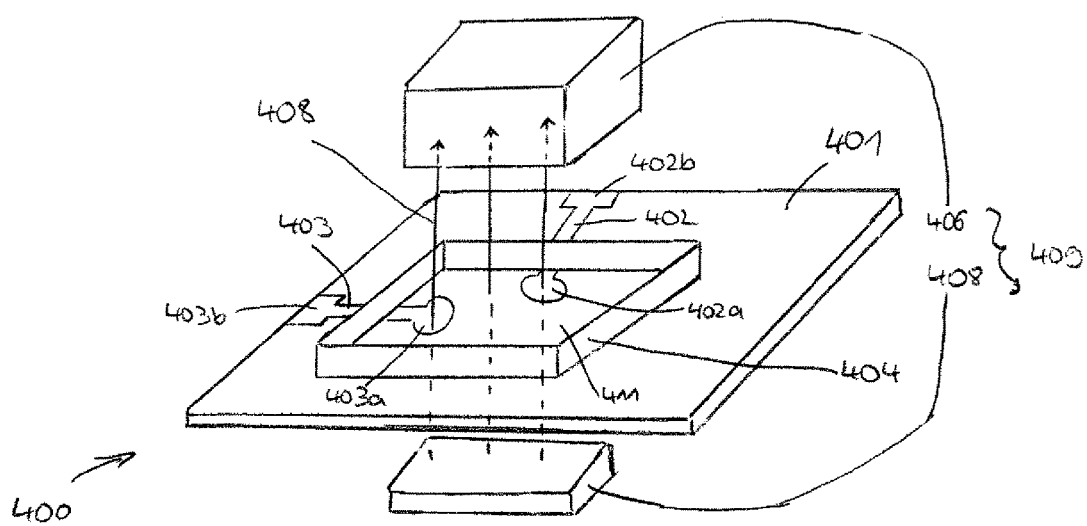
FIG. 4 shows a device for analysing biological substances in a test solution according to a fourth embodiment of the present invention.

FIG. 4 shows a device 400 for analysing biological substances in a test solution according to a fourth embodiment of the present invention. The device 400 comprises a test substrate 401, on which a fluid chamber 404 is formed, for example similarly to the first to fourth fluid chambers 107 to 110 described in the first embodiment in FIG. 1, which chamber surrounds a test region 411 which is formed so as to receive the test solution.

On the test substrate 401, a first electrode 402 and a second electrode 403 are arranged. The first electrode 402 and the second electrode 403 in this case each comprise a contact region 402b and 403b respectively, and each comprise an end region 402a and 403a respectively, which is located inside the test region 411 in each case. The electrodes consist of a transparent and preferably biocompatible, in particular bioinert material, in particular one of the above-described materials.

In this case, the device 400 is placed in a microscope 409, for example a fluorescence microscope, which comprises a light source 408 and an optical system 406 for examining the test region 404. In particular, images or videos of the test region 404 can also be recorded by means of the microscope 409.

The electrodes which are used for the device according to the invention, in particular for the devices described in the above embodiments, can have in particular a hybrid structure, as illustrated in FIGS. 5a to 5d, which are schematic cross-sectional views of electrodes.

Figure 5A:
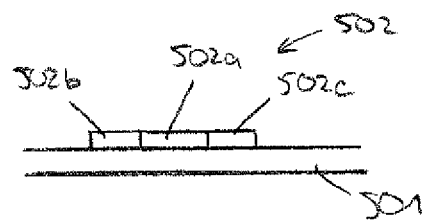

FIG. 5a illustrates a strip-shaped electrode 502 on a test substrate 501. The electrode 502 comprises an inner strip-shaped portion 502a made of a preferably biocompatible or bioinert material. Furthermore, the electrode 502 comprises two outer strip-shaped portions 502b and 502c, which preferably consist of silver nanotubes. In this case, the entire electrode 502 is transparent.

Figure 5B:
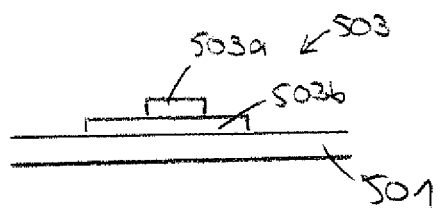

In FIG. 5b, a transparent electrode 503 is illustrated, which comprises a lower strip-shaped region 503b, which is arranged on the test substrate 501 and preferably consists of silver nanotubes. On the lower strip-shaped region 503, a smaller, upper strip-shaped region 503a is arranged, which is preferably made of a biocompatible or bioinert material. The upper strip-shaped region 503a can also be made of a non-conductive material, in particular a polymer.

Figure 5C:
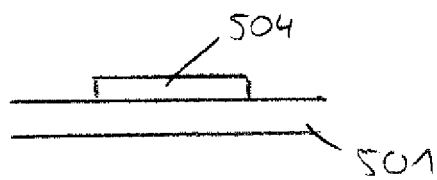

FIG. 5c shows a transparent electrode 504, wherein the material of the electrode 504 itself is a multicomponent material, which for example comprises both silver nanotubes and polymers.

Figure 5D:
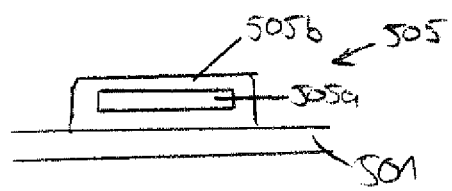

FIG. 5d shows a transparent electrode 505 which comprises an inner conductive, strip-shaped region 505a and an outer strip-shaped region 505b which surrounds said inner region. The outer strip-shaped region 505b in this case preferably consists of a biocompatible or bioinert, but not necessarily conductive, material which is in particular made of polymers such as PDMS or OSTE. In particular, corrosion of the inner strip-shaped region 505a is prevented thereby.

The electrodes used can thus have in particular a biocompatible, electrically insulating protective layer or passivation layer. The hybrid structures of the electrodes which are shown in FIGS. 5a to 5d can also be combined in this case.

FIG. 6 is a flow chart for illustrating a production method for a device for analysing biological substances in a test solution. In a first method step S11, a test substrate which is transparent at least in part is formed so as to receive the test solution. In this case, the test substrate is made of a material which is transparent at least in part, preferably of a plastics material such as PET or COP. The test substrate can also be made of other materials, in particular glass and/or silk and/or paper, in particular also of films and/or plaster.

Preferably, cavities and/or a channel system and/or fluid chambers can be formed in the test substrate in order to receive a microsystem. In this case, a channel system can be engraved into the substrate. On the test substrate, surface functionalisations can also be formed, in particular hydrophobic and/or hydrophilic regions for transporting liquids. Furthermore, surface structurings can be arranged on the test substrate. A pump system for transporting liquids can also be arranged on the test substrate.

In a second method step S12, a plurality of electrodes are arranged on the test substrate. In this case, at least one portion of the electrodes is made of a transparent material. The transparent material includes in particular carbon nanotubes (CNTs) and/or conductive metal oxides (e.g. ZnO) and/or polymers and/or metal nanowires, for example silver nanowires, and/or PEDOT:PSS and/or graphene and/or graphene oxide. The test substrate and the electrodes preferably consist at least in part of a biocompatible, in particular bioinert material. Preferably, the material of the electrodes has no fluorescence or autofluorescence and/or absorption and/or reflection and/or quenching effects such as fluorescence quenching when irradiated with visible light and/or UV light. Preferably, the material of the test substrate and the electrodes is bendable.

The sequence of the method steps is not fixed in this case. Thus forming the test substrate and arranging the electrodes can also take place at the same time.

According to one embodiment, the device can be produced in a single method step by means of 3D printing.

According to additional embodiments, in particular flexible test substrates can be extensively coated with electrode materials at low process temperatures. It is also possible to carry out direct structuring of the conductive layers or the microfluidic structures.

The electrode material, in particular carbon nanotubes, silver nanowires, graphene, polymers or conductive metal oxides such as zinc oxide, are preferably placed in solution for this purpose, for example by means of surfactants. The solution with the electrode material is then applied to the test substrate in order to arrange the electrodes.

In this case, the electrodes can be arranged according to one embodiment by means of an ink-jet printer. In this case, the electrode material is printed and preferably structured on the test substrate.

According to another embodiment, the electrodes can be formed by means of a spraying process. For this purpose, for the structuring, firstly a shadow mask is applied to the test substrate, then the electrode material is sprayed on in solution, and then the shadow mask is removed again. The shadow mask can be produced for example by means of laser-cutting. Optionally, a cleaning step can then take place, which removes in particular surfactants and other non-biocompatible materials. Furthermore, the method can comprise an optional sintering step, for example to increase the electric conductivity.

According to another embodiment, the electrodes can be arranged on the test substrate by means of spin-coating.

The above-mentioned production methods can also be combined as desired.

FIG. 7 is a flow chart for illustrating a method for operating a device for analysing biological substances in a test solution. In this case, the device can be in particular one of the devices described in the above-mentioned embodiments. In a first step S21, the test solution is applied to the test region of the test substrate. The application can be carried out for example by means of a pipette or by means of suitable openings or by means of a channel system. The biological substances, for example cells or cell components, in this case are preferably in suspension in the test solution, in particular a microfluid.

In a second step, impedances of the electrodes are measured. In this case, an alternating voltage is applied between different electrodes so that an electrical field is created between the electrodes in the test region. If the electrical field changes due to a change in the biological substances between the two electrodes, then a frequency-dependent change in the impedances of the electrodes is also measured.

In a third method step S23, the biological substances are then analysed on the basis of the measured impedances of the electrodes.

If for example the impedance on an electrode changes, then it can be inferred that a biological substance is moving in the region of the electrode. As a result, it can be concluded that there is a growth of the biological substance, cell vitality, or a movement of the biological substance.

FIG. 8 is a flow chart for illustrating a method for operating a device for analysing biological substances in a test solution. In this case, the device comprises a plurality of electrodes which each have an end region and a remaining region, wherein the respective end regions of the plurality of electrodes are formed so as to be substantially parallel to one another. The device can thus be in particular a device 200 according to the second embodiment, as shown in FIG. 2.

In parallel with the above-described operating method, in a first step S31, a test solution is applied to the test substrate, and in a second step S32, impedances of the electrodes are measured.

In a third step S33, a propagation speed and/or a growth, in particular a growth speed, of the biological substances in the test solution in a direction which is perpendicular to the parallel rows are determined on the basis of the measured impedances of the electrodes. If for example the impedance of an electrode changes, then it can be inferred that the biological substance is located on said electrode. By measuring the timespan between a first point in time, at which the biological substance is located on a first electrode, and a second point in time, at which the biological substance is located on an adjacent, second electrode, on the basis of the known distance between two adjacent electrodes, the propagation speed and/or the growth, that is to say the growth speed, of the biological substance in a direction which is perpendicular to the electrodes can be calculated.

FIG. 9 is a flow chart for illustrating a method for operating a device for analysing biological substances in a test solution. Analogously to the above-described operating method, in a first step S41, the test solution is applied to the test region of the test substrate, and in a second step S42, impedances of the electrodes are measured. In this case, the electrodes each have an end region and a remaining region, wherein the respective end regions of the electrodes are distributed in a spatially uniform manner, that is to say in particular in an array in the test region of the test substrate. In particular, the operating method is suitable for a device 300 according to the third embodiment, as illustrated in FIG. 3.

In this case, in a third step S43, a spatial and/or temporal distribution of the biological substances in the test solution is determined on the basis of the measured impedance of the electrodes. In this case, when the impedance of an electrode changes, it is concluded that, at the time of the change of the impedance, the biological substances reach, that is to say contact, the end region of the electrode. By measuring the timespan between a first point in time, at which the biological substance is located on an end region of a first electrode, and a second point in time, at which the biological substance is located on an end region of an adjacent, second electrode, on the basis of the known distance between two end regions of the adjacent electrodes, the propagation speed and the spatial and/or temporal distribution of the biological substance in the test solution can be calculated.

The above-mentioned embodiments can also be combined. Thus a device according to one embodiment can comprise both electrodes for determining a spatial and/or temporal distribution of the biological substances, for example in an arrangement as illustrated in FIG. 3, and also electrodes for determining a propagation speed and/or a growth of the biological substances, for example in an arrangement as illustrated in FIG. 2.

The invention claimed is:

1. Device for analysing biological substances in a test solution, comprising a test substrate which is transparent at least in part, consists at least in part of a biocompatible material, and has a test region for receiving the test solution; and a plurality of electrodes which are arranged on the test substrate and extend into the test region, which electrodes each comprise an end region, which consists at least in part of a biocompatible material, and a remaining region, which consists of a material which has a higher electrical conductivity than the biocompatible material of the end region, wherein in each case, at least one portion of the electrodes is made of a transparent material in the test region.

2. Device according to claim 1, wherein the test substrate comprises a cavity for receiving the test solution.

3. Device according to claim 1, wherein the transparent material from which at least the portion of the electrodes is made, includes carbon nanotubes and/or conductive oxides and/or polymers and/or metal nanowires, in particular silver nanowires, and/or PEDOT:PSS and/or graphene and/or graphene oxide.

4. Device according to claim 1, wherein the electrodes consist at least in part of a material which, when irradiated with visible light and/or UV light, has no fluorescence and/or absorption and/or reflection and/or quenching effects.

5. Device according to claim 1, wherein the test substrate and the electrodes consist at least in part of a bendable material.

6. Device according to claim 1, wherein the electrodes each comprise the end region and the remaining region; and wherein the end regions of at least two electrodes are arranged in rows which are substantially parallel to one another in the test region.

7. Method for operating a device according to claim 6, comprising the steps of:
applying the test solution to the test region of the test substrate,
measuring impedances of the electrodes,
determining a propagation speed and/or growth of the biological substances in the test solution in a direction which is perpendicular to the parallel rows on the basis of the measured impedances of the electrodes.

8. Device according to claim 1, wherein the electrodes each comprise the end region and the remaining region; and wherein the respective end regions of at least two of the electrodes are arranged in the test region so as to be distributed in a spatially uniform manner, in particular in an array.

9. Method for operating a device according to claim 8, comprising the steps of:
applying the test solution to the test region of the test substrate,
measuring impedances of the electrodes,
determining a spatial and/or temporal distribution of the biological substances in the test solution on the basis of the measured impedances of the electrodes.

10. Method for operating a device according to claim 1, comprising the steps of:
applying the test solution to the test region of the test substrate,
measuring impedances of the electrodes, and
analysing the biological substances on the basis of the measured impedances of the electrodes.

11. Device according to claim 1, wherein at least one of the biocompatible material of the test substrate and the biocompatible material of the end region is a bioinert material.

12. Production method for a device for analysing biological substances in a test solution, comprising the steps of:
forming a test substrate which is transparent at least in part and consists at least in part of a biocompatible material with a test region for receiving the test solution; and
arranging a plurality of electrodes on the test substrate, which each comprise an end region, which consists at least in part of a biocompatible material, and a remaining region, which consists of a material which has a higher electrical conductivity than the biocompatible material of the end region;
wherein in each case, at least one portion of the electrodes is made of a transparent material in the test region.

13. Production method according to claim 12, wherein the electrodes are arranged by means of a spraying process and/or spin-coating and/or an ink-jet printing process and/or 3D printing.

14. Production method according to claim 12, wherein at least one of the biocompatible material of the test substrate and the biocompatible material of the end region is a bioinert material.

* * * * *